United States Patent [19]
Chan et al.

[11] Patent Number: 5,131,984
[45] Date of Patent: Jul. 21, 1992

[54] HIGH QUALITY PHENOL RECTIFICATION WITH ENERGY RECOVERY

[75] Inventors: Chong H. Chan, Richmond; William B. Fisher, Chester, both of Va.; Joseph D. Shrom, Holland, Pa.

[73] Assignee: Allied-Signal Inc., Morris Township, Morris County, N.J.

[21] Appl. No.: 764,278

[22] Filed: Sep. 23, 1991

[51] Int. Cl.$^5$ .................. B01D 3/34; C07C 37/74
[52] U.S. Cl. .......................... 203/6; 203/21; 203/75; 203/76; 203/77; 203/87; 203/91; 203/DIG. 8; 203/DIG. 19; 568/749; 568/754
[58] Field of Search .......... 203/87, 6, 21, 27, 29, 203/DIG. 19, 91, 92, 99, 4, 74, 75, 76, 77, 81, 82, 83, DIG. 8; 568/754, 749

[56] References Cited

U.S. PATENT DOCUMENTS

| | | | |
|---|---|---|---|
| 2,910,511 | 10/1959 | Joris | 203/DIG. 19 |
| 2,992,169 | 7/1961 | Gregory et al. | 568/754 |
| 3,168,451 | 2/1965 | Gorand | 203/21 |
| 3,265,590 | 8/1966 | Redcay | 203/21 |
| 3,654,094 | 4/1972 | Yamagishi et al. | 203/87 |
| 3,846,255 | 11/1974 | Sisk | 568/749 |
| 4,108,914 | 8/1978 | Gewartowski | 203/87 |
| 4,351,967 | 9/1982 | Nishimura et al. | 568/754 |
| 4,634,796 | 1/1987 | Suciu et al. | 568/754 |
| 4,832,796 | 5/1989 | Fulmer | 568/754 |

Primary Examiner—Wilbur Bascomb, Jr.
Attorney, Agent, or Firm—William H. Thrower

[57] ABSTRACT

The process for rectification of phenol prepared from crude phenol being the product of decomposition of cumene hydroperoxide and having previously been distilled to remove large portions of acetone, cumene and alpha methylstyrene which includes:
  feeding the column overhead vapors to a condenser, thereby condensing a major portion of the overhead vapors;
  withdrawing a small portion of the overhead vapors from the condenser while still in a vapor state, the small portion being relatively enriched in lights and laden with light acids;
  returning the condensate from the condenser to the phenol distillation column as reflux; and
  withdrawing product phenol from at least one-theoretical stage below the top of the phenol distillation column, the product phenol having improved clarity when dispersed in water, clarity being at least 93 percent light transmission as measured by an electrophotometer in a water light test. It is preferred that the condenser in step (c) is a steam generating condenser, thereby condensing a major portion of the vapors while vaporizing water circulating through the steam generating condenser to produce steam.

10 Claims, 1 Drawing Sheet

HIGH QUALITY PHENOL RECTIFICATION WITH ENERGY RECOVERY

BACKGROUND OF THE INVENTION

1. Field of the Invention

The invention is directed to a process for phenol rectification at a sufficiently high temperature level to recover the heat of condensation for steam generation while reducing undesirable impurities in product phenol.

2. Description of Related Art

This invention relates to a method to prepare phenol from the products of decomposition (cleavage) of cumene hydroperoxide. Cumene hydroperoxide is decomposed to yield various product components including phenol and acetone under acidic catalysis.

The decomposition product is neutralized, typically in an alkaline ion exchanger, before being separated into product phenol, byproducts and unreacted cumene for recycle. The ion exchange beds are operated in cycles, between regenerations, and the neutralization operation is controlled to hold the pH of the decomposition mass in the range of 2 to 4. A wide variety of byproduct organic acids in considerable amount remain in the neutralized decomposition crude product. Common organic acids in the neutralized decomposition mass include benzoic acid, formic acid, acetic acid, maleic acid, lactic acid, propionic acid, isobutyric acid, oxalic acid, succinic acid, valeric acid, and isovaleric acid. The total acidity, under normal operating conditions, is in the range of 50-500 ppm, but typically falls between 150 and 300 ppm. The sources of the acidity are likely to be the oxidized fractions of cumene molecules and impurities in the feed stocks.

The decomposition mass is separated sequentially into acetone, cumene, alpha methyl styrene (AMS), phenol and high boiling residues. Phenol, acetone and AMS are further purified into end products. Recovered cumene is caustic washed to rid it of acidity before being recycled to oxidation. The separation of the crude decomposition mass is carried out in a series of fractionating distillation columns in commercial operation. Thus substantial portions of acetone, cumene and AMS are removed by distillation, with a resulting crude phenol mass which can be rectified to obtain product-grade phenol. Significant amounts of acid containing compounds evade front end distillation and enter the phenol purification column with the crude phenol mass, where acids are released under vacuum and elevated temperature conditions.

Purification of the crude phenol mass is carried out in a vacuum distillation column usually equipped with from 30 to 40 vapor-liquid counter current contact trays or equivalent effective height of mass transfer packed beds. The vacuum level in the distillation column overhead ranges from 50 to 300 mmHg. The overhead vapors are withdrawn from the column and totally condensed. To reduce light impurities in the product phenol, a small fraction of the condensed overhead is removed from the phenol purification column and recycled upstream. This recycle stream can vary from 3 to 15 weight percent of the total overhead condensate. The balance of the overhead condensate is returned to the column to provide reflux. Product phenol is withdrawn from a few trays below the overhead.

The acidity in the top of the phenol purification column acts as catalyst to generate impurities affecting phenol quality. On the merchant market water light transmission, a measure of the amount of water insoluble organic compounds, is the prevailing specification for phenol sales. The acid catalyzed products have been proven to be responsible for phenol failing the water light test. In the use of phenol for the manufacture of cyclohexanone by hydrogenation, acids have been found to be poisonous to the palladium catalyst.

Thus, it is desirable to develop a process for achieving sales grade phenol in an economic manner. U.S. patent application Ser. No. 650,253, filed Feb. 4, 1991 discloses a method wherein injection of water into the overhead of the phenol distillation column has been successful in improving the water light transmission of the phenol product. Water injection has the apparent effect of reducing acidity and light impurities in phenol and mitigating any acid catalyzed reactions. However, water injection lowers the column overhead temperature substantially. This prevents the use of the overhead condenser to generate low pressure steam. At the overhead pressure of 150 mmHg, a typical condition for the phenol purification column, the condensing phenol temperature is around 130° C., suitable for generating 10 psig. steam for a variety of process and utility uses. With water injection in sufficient amount to attain a water concentration level necessary for product passing the water light test, the corresponding condensing temperature falls below 60° C., ruling out steam generation. The value of steam generation is considerable. Steam generation can recover substantially all the energy input to the distillation operation, although at a lower pressure level.

SUMMARY OF THE INVENTION

The process for rectification of phenol, said phenol prepared from crude phenol being the product of decomposition of cumene hydroperoxide and having previously been distilled to remove large portions of acetone, cumene and alpha methylstyrene, comprising:

(a) introducing said crude phenol as a feed to a fractional distillation column at or near to the bottom;

(b) providing sufficient heat to said phenol distillation column to vaporize the phenol and lower boiling components of the crude phenol;

(c) withdrawing the overhead vapors from the column overhead and feeding said overhead vapors to a condenser, thereby condensing a major portion of said vapors;

(d) withdrawing a small portion of said overhead vapors from said condenser while still in a vapor state, said small portion being relatively enriched in lights and laden with light acids;

(e) returning the condensate from said condenser to the phenol distillation column as reflux; and (f) withdrawing product phenol from at least one theoretical stage below the top of the phenol distillation column, said product phenol having improved clarity when dispersed in water, said clarity being at least 93 percent light transmission as measured by an electrophotometer in a water light test.

Also, it is preferred that the condenser in step (c) is a steam generating condenser, thereby condensing a major portion of said vapors while vaporizing water circulating through the steam generating condenser to produce steam.

DESCRIPTION OF THE PREFERRED EMBODIMENT

Figure 1:
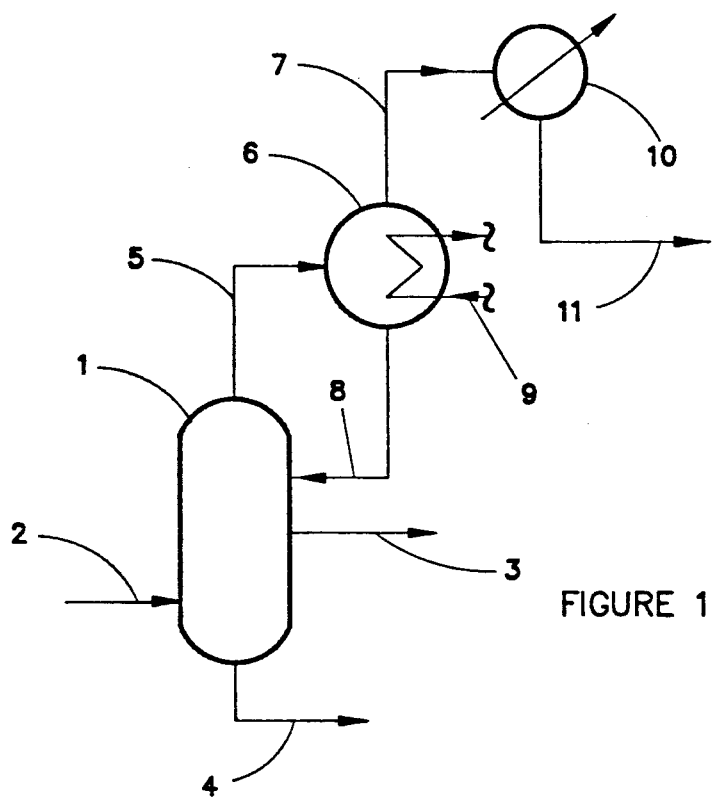
FIG. 1 represents a schematic diagram of a first embodiment of the process of the invention, described below.

The process of the invention serves to remove acids in the phenol purification column at a temperature level for the overheads which is suitable for generating low pressure steam in the overhead condenser. The embodiment of this invention entails modifications of the phenol purification column overhead system. In a first embodiment illustrated in FIG. 1, referred to as the acid purge method hereafter, vessel 1 is a vacuum distillation column, preferably 30 to 40 vapor-liquid counter current contact trays. Crude phenol is fed near to the bottom tray through line 2 in the lower one third of the column. This crude phenol feed is obtained by the decomposition of cumene hydroperoxide, then sequential distillation of the decomposition mass to remove substantial portions of acetone, cumene and AMS. Refined phenol product is withdrawn through line 3 from at least one theoretical stage below the top of the distillation column, preferable 3 to 10 trays below the overhead, within the upper one third of the column. The bottoms withdrawn through line 4 can be sent to a phenol recovery unit. The column overhead vapors are withdrawn through line 5 and fed to a condenser, preferably a steam generating condenser 6 in which it is condensed while heating boiler feed water circulating through line 9. A small portion of the overhead vapor, ranging from one to eight percent of weight of the phenol product rate (line 3) is left uncondensed by control of the condenser and is withdrawn through line 7.

This stream is relatively enriched in lights and laden with light acids and is condensed in a second condenser 10 commonly referred to as a vent condenser. The condensate from the vent condenser 10 is purged from the phenol purification column and may be sent through line 11 to a separate phenol recovery unit or may be recycled back to the cumene recovery column (not shown) in the case where water is present in the cumene column. The presence of water in the cumene column causes a phase split in the condensate of the column overhead vapor and the light acids are extracted into the water phase which is decanted and removed from the still train. The overhead condensate from the steam generating condenser 6, substantially purified by the removal of the light acids and impurities through line 7, is fed back through line 8 to the column at the top as reflux. Acids and light impurities in the phenol product obtained by this method are substantially reduced.

Figure 2:
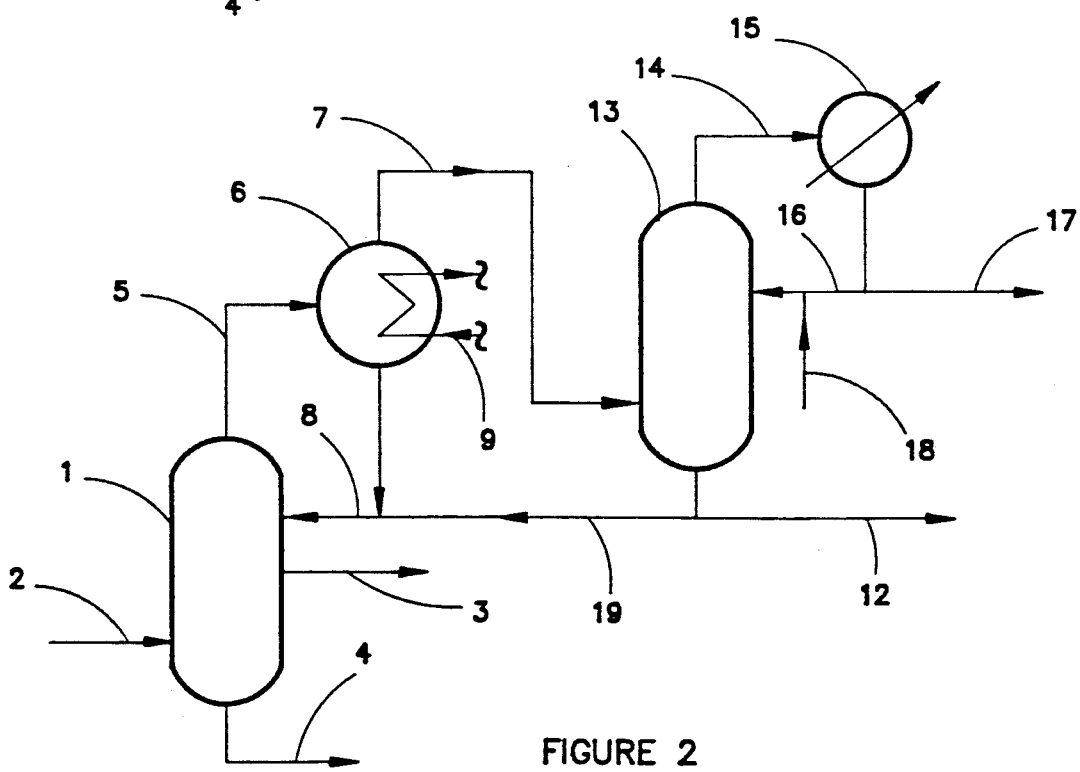
FIG. 2 represents a schematic diagram of a second embodiment of the process of the invention, described below.

A second embodiment, referred to as the acids stripping method, is illustrated in FIG. 2. In this embodiment, a larger portion of the column overhead vapor withdrawn through line 5, ranging from five to fifteen percent of the weight of the phenol product rate (line 3), remains uncondensed in the steam generating condenser 6 and is fed via line 7 to the lower part of a distillation column equipped with ten to twenty vapor-liquid contact trays or equivalent height of mass transfer packed beds. Water is injected via line 18 into the overhead of acids stripping column 13 to suppress the formation of acid catalyzed reaction products. Overhead vapors, loaded with light acids, is removed via line 14 to condenser 15. A portion of this condensate is returned as reflux via line 16, the remaining portion is sent via line 17 to a separate phenol recovery unit. The column 13 bottoms, dried and free of light acids, is partly refluxed to the top of the phenol purification column via line 19 and partly recycled via line 12 upstream in the still train, preferably to the cumene recovery column (not shown) for recovering cumene and alpha-methylstyrene. The condensate from the steam generating condenser 6 is totally returned to the top of the phenol purification column 1 as reflux, as in the first embodiment.

In general, the overhead pressure for the distillation column in the embodiments described above may range from 50 to 300 mmHg while the required reflux ratio may be controlled between 0.5 and 1.0. When it is desired to produce steam, the overhead pressure is preferred to be at least 130 mmHg. This will be adequate to produce useful low pressure steam. However, the column bottom temperature should not exceed 175° C. in order to prevent potential product degradation brought about by cracking of high boiling impurities.

The test for clarity in water of phenol has been called the water light transmission (WLT) or water solubility test, described at column 1, lines 52–59 of U.S. Pat. No. 2,910,511. The following procedure was followed to determine WLT:

Procedure—Water Light Transmission Test (1) Into two 100-milliliter cylinders, measure 75 milliliters of distilled water at 25° C. Pipet 5 milliliters of phenol sample, at 55° to 60° C., into one of the cylinders. Place stopper, shake vigorously and allow to stand for ten minutes at 25° C.

(2) Compare the clarity of the sample solution with that of the distilled water. Do this by looking through the sides of the cylinders which are held about three feet from a window in such a manner that the line of sight is against the vertical dark surface below the sill. The light should be north light and sunlight glare must be avoided. Artificial light should come from a "daylight" lamp in such a manner as to simulate the above condition.

(3) Remove the stopper from the cylinder, tilt the cylinder slightly at various angles and observe the surface of the liquid for an oil separation.

(4) If the sample solution is not clear and when the degree of cloudiness is to be determined by a photometer, transfer 60 milliliters at 25° C., to the absorption cell and determine the percent light transmission, using 60 milliliters of distilled water in the reference cell.

(5a) If the sample solution is clear and no oil is observed on the surface, report as "clear at 25° C."

(5b) If the sample solution is cloudy and/or shown any separated oil, report the degree of cloudiness as "slightly-hazy - hazy - cloudy - opaque" and the oil present as "trace" or "oil present" dependent upon the amount.

(5c) If the degree of cloudiness was determined by the electrophotometer, report the percent light transmission. Less than 93 percent light transmission is not water clear.

EXAMPLE 1

Refer to FIG. 1 Vessel 1 is a vacuum distilled column equipped with 32 trays. Crude phenol, stream 1, was fed near to the bottom tray. Refined phenol product, line 3, was withdrawn from the third or the fifth tray below the top of the column. The bottoms, stream 4, were sent to a phenol recovery unit. In what is to be referred to as mode A operation, the prior process, the column overhead was withdrawn through line 5 and fed to a steam generating condenser, vessel 6, in which it was condensed while heating boiler feed water, circulating through line 9. A small portion of the overhead condensate, ranging from one to eight percent of the product (line 3) rate, was removed from the condensate and sent to a lights recovery unit elsewhere in the process. This side stream serves the purpose of reducing the lights content of product phenol. The remainder and the bulk of the overhead condensate, stream 8, is fed back to the column at the top as reflux. In what is to be referred to as mode B operation, an embodiment of method 1 of this invention, a portion of the overhead vapor was withdrawn through line 7, equivalent to one to eight percent of the product (line 3) rate, and was left uncondensed by control of the steam generating condenser 6. The overhead vapor withdrawn through line 7, relatively enriched in lights and laden with light acids was condensed in a vent condenser, vessel 10, and sent to a lights recovery unit. The purified condensate from the steam generating condenser is returned to the top tray of the column as reflux.

The segregation of the uncondensed overhead vapor through line 7 from the column reflux brings about the reduction of not only the lights content of the phenol product but also the light acids which cause the formation of undesirable by-products in the overhead. The invention is based on the efficacy of mode B operation in producing merchant grade phenol while mode A, the standard practice, allows production of phenol suitable for special applications only.

A test, referred to as water light test, is used to screen phenol product for merchant sales. In this test, 5 parts of the phenol product are added to 75 parts of distilled water. The mixture is brought to 25° C. and subjected to light transmittance measurement by a photometer calibrated to read 100% for distilled water. Light transmittance of 93% or better qualifies the product for general merchant sales. Percent light transmittance, or water light, as it is commonly called, is a measure of phenol purity. The presence of undesirable impurities which are typically water insoluble reduces the light transmittance.

Table 1 presents the monthly averages of the "water light" number of the phenol produced for 19 months while under mode A operation and the corresponding values for the phenol product for 4 months after mode B operation was implemented and proper control was achieved.

TABLE 1

WATER LIGHT COMPARISON, MODE A OPERATION VS MODE B OPERATION

|  | MONTH | AVERAGE VALUES, WATER LIGHT | AMS IMPURITIES (PPM) |
|---|---|---|---|
| MODE A | 1 | 21.7 | 566 |
|  | 2 | 30.9 | 561 |
|  | 3 | 23.1 | 726 |
|  | 4 | 29.8 | 584 |
|  | 5 | 45.3 | 585 |
|  | 6 | 30.6 | 549 |
|  | 7 | 28.0 | 575 |
|  | 8 | 26.7 | 934 |
|  | 9 | 27.3 | 856 |
|  | 10 | 16.7 | 787 |
|  | 11 | 14.2 | 676 |
|  | 12 | 79.0 | 1173 |
|  | 13 | 9.0 | 934 |
|  | 14 | 24.0 | 1547 |
|  | 15 | 80.0 | 485 |
|  | 16 | 38.9 | 404 |
|  | 17 | 52.7 | 486 |
|  | 18 | 45.2 | 590 |
|  | 19 | 44.3 | 1040 |
| MODE B | 1 | 90.1 | 114 |
|  | 2 | 92.7 | 93 |
|  | 3 | 93.3 | 161 |
|  | 4 | 90.3 | 403 |

Operating under Mode A, no merchant grade material produced.

Under Mode B, approximately 75% of the material produced was merchant grade.

EXAMPLE 2

To demonstrate the use and benefits of the second embodiment covered in this invention, a computer simulation of the effects of the purge rate on the acidity level is presented in the following. The corresponding effects on the steam generating capacity of the condenser are also presented. In the simulation calculations, the acidity in the feed is assumed to be 33 ppm as acetic acids. The feed contains 94.5% of phenol by weight and the phenol content in the bottoms is held at 80% by weight. The column overhead is controlled at 150 mmHg. Case A in this example corresponds to mode A operation as referred to in the preceding example. Case B represents mode B operation as described in Example 1. Case C illustrates an implementation of method 2 of this invention. In case C, an increased amount of the column overhead is left uncondensed in the steam generating condenser enabling enhanced acid removal. This enhanced acid removal operation may be implemented when either very low acidity level in the overhead becomes desirable or when the acidity in the feed should become higher than usual. Table 2 presents the calculated results.

TABLE 2

| CASE | % PURGE (OF PRODUCT RATE | STEAM GENERATING CAPACITY % | ACIDITY IN OVERHEAD PPM | ACIDS[1] IN PRODUCT PPM |
|---|---|---|---|---|
| A | 5.8 | 100 | 735 | 40-50 |
| B | 5.8 | 96 | 102 | 20-25 |
| C | 12.5 | 90 | 47 | 10-15 |

[1] Formic, Acetic, Lactic, Propionic, Isobutyric

We claim:

1. The process for rectification of phenol, said phenol prepared from crude phenol being the product of decomposition of cumene hydroperoxide and having previously been distilled to remove substantial portions of acetone, cumene and alpha methylstyrene, comprising:

(a) introducing said crude phenol as a feed to a fractional distillation column;

(b) providing sufficient heat to said phenol distillation column to vaporize the phenol and lower boiling components of the crude phenol;

(c) withdrawing overhead vapors resulting from step (b) from the column overhead and feeding said overhead vapors to a condenser, thereby condensing a major portion of said vapors;

(d) withdrawing a small portion of said overhead vapors from said condenser while still in a vapor state, said small portion being relatively enriched in lights and laden with light acids;

(e) returning condensate resulting from step (c) from said condenser to the phenol distillation column as reflux; and (f) withdrawing product phenol from at least one theoretical stage below the top of the phenol distillation column, said product phenol having improved clarity when dispersed in water, said clarity being at least 93 percent light transmission as measured by an electrophotometer in a water light test.

2. The process of claim 1 wherein said condenser in step (c) is a steam generating condenser, thereby condensing a major portion of said vapors while vaporizing water circulating through the steam generating condenser to produce steam.

3. The process of claim 2 wherein the pressure at the top of the distillation column is at least 130 mmHg and the temperature of the bottoms is no greater than 175° C.

4. The process of claim 3 wherein in step (d) said small portion of said overhead vapors withdrawn from said condenser is equal to from 1 to 15 percent of the weight of product phenol withdrawn in step (f).

5. The process of claim 4 wherein the reflux ratio is controlled between 0.5 and 1.0.

6. The process of claim 5 wherein the crude phenol feed to the distillation column is in the lower one third of the column and the product phenol is withdrawn from the upper one third of the column.

7. The process of claim 6 wherein said small portion of overhead vapors withdrawn from the steam generating condenser is condensed in a vent condenser and purged.

8. The process of claim 7 wherein in step (d) said small portion of said overhead vapors withdrawn from said condenser is equal to from 1 to 8 percent of the weight of product phenol withdrawn in step (f).

9. The process of claim 6 wherein said small portion of overhead vapors withdrawn from the steam generating condenser is fed to the lower part of an acids stripping distillation column, overhead vapor is withdrawn from said acids stripping column and condensed, a portion of the resulting condensate is returned to the acids stripping column as reflux while the remaining portion is purged, sufficient water is injected into said reflux to suppress the formation of acid catalyzed reaction products, and a portion of bottoms from said acid stripping column, dried and free of light acids, is returned to the phenol distillation column as reflux while the remaining portion of the bottoms is withdrawn.

10. The process of claim 9 wherein in step (d) said small portion of said overhead vapors withdrawn from said condenser is equal to from 5 to 15 percent of the weight of product phenol withdrawn in step (f).

* * * * *